United States Patent
Mangione-Smith (10) Patent No.: US 8,434,674 B2
(45) Date of Patent: May 7, 2013

(54) FIDUCIAL MARKERS FOR AUGMENTED REALITY

(75) Inventor: William H. Mangione-Smith, Kirkland, WA (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/058,831

(22) PCT Filed: Jul. 29, 2010

(86) PCT No.: PCT/US2010/043633
§ 371 (c)(1),
(2), (4) Date: Feb. 11, 2011

(87) PCT Pub. No.: WO2012/015405
PCT Pub. Date: Feb. 2, 2012

(65) Prior Publication Data
US 2011/0186625 A1    Aug. 4, 2011

(51) Int. Cl.
*G06F 17/00*    (2006.01)
(52) U.S. Cl.
USPC .......................................... 235/375; 235/468
(58) Field of Classification Search .................. 235/375, 235/468; 705/51
See application file for complete search history.

(56) References Cited

U.S. PATENT DOCUMENTS

| | | | |
|---|---|---|---|
| 6,542,083 B1 | 4/2003 | Richley et al. | |
| 2003/0046240 A1* | 3/2003 | Stone et al. | 705/51 |
| 2005/0240484 A1* | 10/2005 | Yan et al. | 705/26 |
| 2006/0050929 A1 | 3/2006 | Rast et al. | |
| 2006/0215147 A1 | 9/2006 | Scott et al. | |
| 2007/0098234 A1 | 5/2007 | Fiala | |
| 2008/0138604 A1 | 6/2008 | Kenney et al. | |
| 2008/0266323 A1 | 10/2008 | Biocca et al. | |
| 2009/0065583 A1 | 3/2009 | McGrew | |

OTHER PUBLICATIONS

Arsenault, A., "Photonic Crystals Security Devices," GOA Brand Protection Conference, Opalux, Feb. 26, 2009.

International Search Report and Written Opinion for International Application No. PCT/US2010/043633 mailed on Nov. 4, 2010.

Kuan, Gary M. et al., "Picometer Level Modeling of a Shared Vortex Double Corner Cube in the Space Interferometry Mission Kite Testbed," Pasadena, CA : Jet Propulsion Laboratory, National Aeronautics and Space Administration, 2006. Astronomical Telescopes and Instrumentation, Probing the Universe from Ground and Space, Orlando, Florida, May 24-31, 2006. Found online at: http://trs-new.jpl.nasa.gov/dspace/bitstream/2014/40134/1/06-1402.pdf, May 24, 1006.

(Continued)

*Primary Examiner* — Ahshik Kim
(74) *Attorney, Agent, or Firm* — Maschoff Brennan (57) ABSTRACT

Fiducial markers for augmented reality are provided. A fiducial marker can be located on an object in the environment and includes retroreflectors that reflect light back towards the source of the light. A portion of the fiducial marker is masked or obscured to form a pattern in the fiducial marker including a reflective portion and a less or non-reflective portion. The pattern of the reflective portion and the less or non-reflective portion stores data that can be read by a reading device and used to generate computer-generated content that is included in an augmented image.

26 Claims, 5 Drawing Sheets

OTHER PUBLICATIONS

Zhao, Feng et al., "Development of sub-nanometer racetrack laser metrology for external triangulation measurement for the space interferometry mission," American Society of Precision Engineering Annual Meeting, Arlington, VA, USA, Nov. 10, 2001. Found online at: http://trs-new.jpl.nasa.gov/dspace/bitstream/2014/13349/1/01-2169.pdf, Nov. 10, 2001.

CS 348C—Topics in Computer Graphics. Stanford University. Fiduciary markers in motion capture. Found online at: http://graphics.stanford.edu/courses/cs348c-97-winter/project.html, Feb. 19, 2006.

Berrou, C. et al., "Near Shannon limit error-correcting coding and decoding: Turbo codes," In Proceedings of the IEEE International Communications Conference (1993), pp. 1064-1070, 1993.

Harle, Robert et al., "Cluster Tagging: Robust Fiducial Tracking for Smart Environments," Computer Laboratory University of Cambridge. Found online at: http://www.cl.cam.ac.uk/research/dtg/www/publications/public/rkh23/ClusterTaggingLoCA2006.pdf, Feb. 11, 2011.

Kim, Hwi et al., "Optimal design of retroreflection corner-cube sheets by geometric optics analysis," (Journal Paper), SPIE 2007, Optical Engineering 46(09), 094002, Sep. 2007.

Krauss, T. F. et al., "Two-dimensional photonic-bandgap structures operating at near-infrared wavelengths", Nature, (Oct. 24, 1996), 383 (6602): 699-702, Sep. 2004.

Hong, Y.K., "Design, fabrication and test of self-assembled optical corner cube reflectors," J. Micromech. Microeng. 15 663-672, Sep. 2004.

Erickson, B.J. et al., "Correlation of single photon emission CT with MR image data using fiduciary markers," American Journal of Neuroradiology, vol. 14, Issue 3 713-720, 1993.

* cited by examiner

FIDUCIAL MARKERS FOR AUGMENTED REALITY

BACKGROUND

Augmented reality often describes a view or image of a real-world environment that has been augmented with computer-generated content. Combining an image of the real-world with computer-generated content has proven useful in many different applications. Advertising, navigation, military, tourism, education, sports, and entertainment are examples of areas where augmented reality can be used.

Merging the image of the real-world environment with the computer-generated content results in an augmented image. Successfully merging the real-world image with the computer-generated content, however, often depends on how well the real-world image is recognized. For example, successfully augmenting an image of a monument can depend on whether the monument is recognized by the device displaying the image of the monument. More specifically, merging computer-generated content such as the name of the monument, location, creator, etc., may depend on the whether the monument in the image is recognized. If the monument is not recognized or known, providing the computer-generated content becomes a very difficult proposition.

One way to recognize objects in images or real-world objects is through the use of fiducial markers. Conventionally, a fiducial marker is an object that is used in the field of view of an imaging system and which appears in the resulting image. In other words, conventional markers are usually used as markers in images and not as markers on real-world objects.

Often, the appearance of fiducial markers in images serves as a reference for image scaling. For instance, fiducial markers at known locations in an image can be used to determine the relative scale of the image. Certain cameras can produce reseau crosses as reference marks in an image. Fiducial markers can also be used to make features of an image more visible. Motion capture applications, for instance, use fiducial markers to track the motion of a marked subject. Fiducial markers in images can also allow independent images to be correlated.

The use of fiducial markers in augmented reality, unfortunately, is quite limited and, as previously stated, fiducial markers are typically found in the image and not on real-world objects.

Although there may be some instances of real-world objects that have fiducial markers, these markers are difficult to recognize. Recognizing fiducial markers at medium and long distances is particularly troublesome. Further, conventional fiducial markers are unable to store significant amounts of data that can be converted to or used to generate computer-generated content in augmented reality applications.

SUMMARY

Embodiments disclosed herein relate to fiducial markers. Fiducial markers store data that can be used to augment an image with computer-generated content. In an illustrative embodiment, a fiducial marker may include a sheet of a material and can be attached to an object. The material is also configured to reflect electromagnetic radiation. A mask is applied to the material to obscure a first portion of the material and not obscure a second portion of the material. The first and second portions of the material store data to be read by a reading device.

In an illustrative embodiment, a fiducial marker may include material that can be attached to an object in an environment. The material includes a first portion with retroreflectors that are configured to reflect electromagnetic radiation received from a device back towards the device. A second portion of the material is less or non-reflective. The first and second portions are arranged to form a pattern and to store data in the fiducial marker. Electromagnetic radiation reflected by the material is modulated according to the pattern. The reflected electromagnetic radiation can be detected and read by a reading device that emitted the electromagnetic radiation.

In another illustrative embodiment, a method for augmenting a real-world image with a computer-generated image includes emitting a light beam towards a fiducial marker located on a real-world object. A reflected light beam includes data stored by the fiducial marker can is read. from the fiducial marker is read by the device that emitted the light beam. Computer-generated content is then generated using the data stored in the reflected light beam and an augmented image, which includes the computer-generated content, is displayed on a display of the device.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Embodiments disclosed herein relate to fiducial markers including fiducial markers for augmented reality applications. In augmented reality, fiducial markers can be embodied as tags that are placed in space or in the environment to assist in object recognition, object tracking, and/or object modeling. Embodiments of the fiducial markers disclosed herein, by way of example and not limitation, support active interrogation, are recognizable at comparatively longer distances, are less obvious to ordinary inspection, and/or are able to store significantly more data or enable access to significantly more data.

Some embodiments of the fiducial markers disclosed herein include retroreflectors. Retroreflectors reflect light back towards the source of the light. As a result, multiple devices can read the fiducial markers from multiple directions. Fiducial markers that incorporate retroreflectors can be configured to store or encode data that can be read or interrogated by a properly configured device. By interrogating the fiducial marker, the data stored or encoded in the fiducial marker can be read or retrieved.

The retroreflectors in the fiducial marker can be partially masked or otherwise obscured in order to encode or store data in the fiducial marker. The pattern of the mask formed in or on the fiducial marker can be one dimensional or multi-dimensional. As a result, fiducial markers that support focused scanning read out allow for an increase in the storage factor. In other words, the amount of information that can be stored in the fiducial marker can be increased for a given size or area based on how the data is stored and/or on how the data is read.

Fiducial markers can be unobtrusively placed on objects in the environment. Thus, at least some embodiments of the fiducial markers are attached to real-world objects rather than only located in the resulting image. Devices that read these fiducial markers can generate augmented reality images using the data stored in the fiducial markers or made accessible by the fiducial markers. In addition, other components of the device (compass, global positioning sensor, etc.) can be used in combination with data read from the fiducial marker to generate and display an augmented reality image.

The fiducial marker generally includes a sheet of material (e.g., molded plastics, semiconductor materials, printed paper, optical reflector, radio frequency reflector) that is attached to an object and configured to reflect electromagnetic radiation. The sheet of material may have a mask applied or affixed thereto that obscures a portion of the reflective material. The mask may take the form of any material that blocks or obscures the reflected electromagnetic radiation, such as grease, a metal shield, optically opaque paper, or dirt. The mask may be applied intentionally or inadvertently. The mask may be applied with an adhesive, stable, nail, rivet, glue, mechanical attachment such as Velcro, or other techniques.

In some instances, the mask can be rearranged (e.g., removed, reoriented, replaced with a new mask) such that the fiducial marker stores new information. For example, the sheet of material may include reflective material. The mask can be made separately such that the stored data changes because the pattern is changed by placing a new mask over the reflective material Alternatively, some areas on the sheet of material may be devoid of reflective components. Thus, the sheet of material has reflective portions and less or non-reflective portions. Together, the reflective and non-reflective portions can be arranged to store data that can be read by a reading device. As previously stated, the mask can be formed by an additional material that obscures the underlying reflective material or by forming the sheet of the material such that certain portions do not include or have reflective properties. In another example, the non-reflective portions can be formed by damaging selected areas of the reflective portion. The damaged portion is an example of a mask.

In some instances, the sheet of material can be used to create multiple fiducial markers. The sheet of material is then diced to form the individual fiducial markers, which are then packaged as necessary or otherwise prepared for deployment.

In another example, the fiducial marker can be directly applied to an object, such as by painting the fiducial marker with retro reflective paint according to a pattern. A template with a pattern formed therein may be provided. The template can be held against the object and paint with retroreflective materials can be applied to the template. When the template is removed, the paint on the object forms the fiducial marker according to the pattern of the template.

Figure 1:
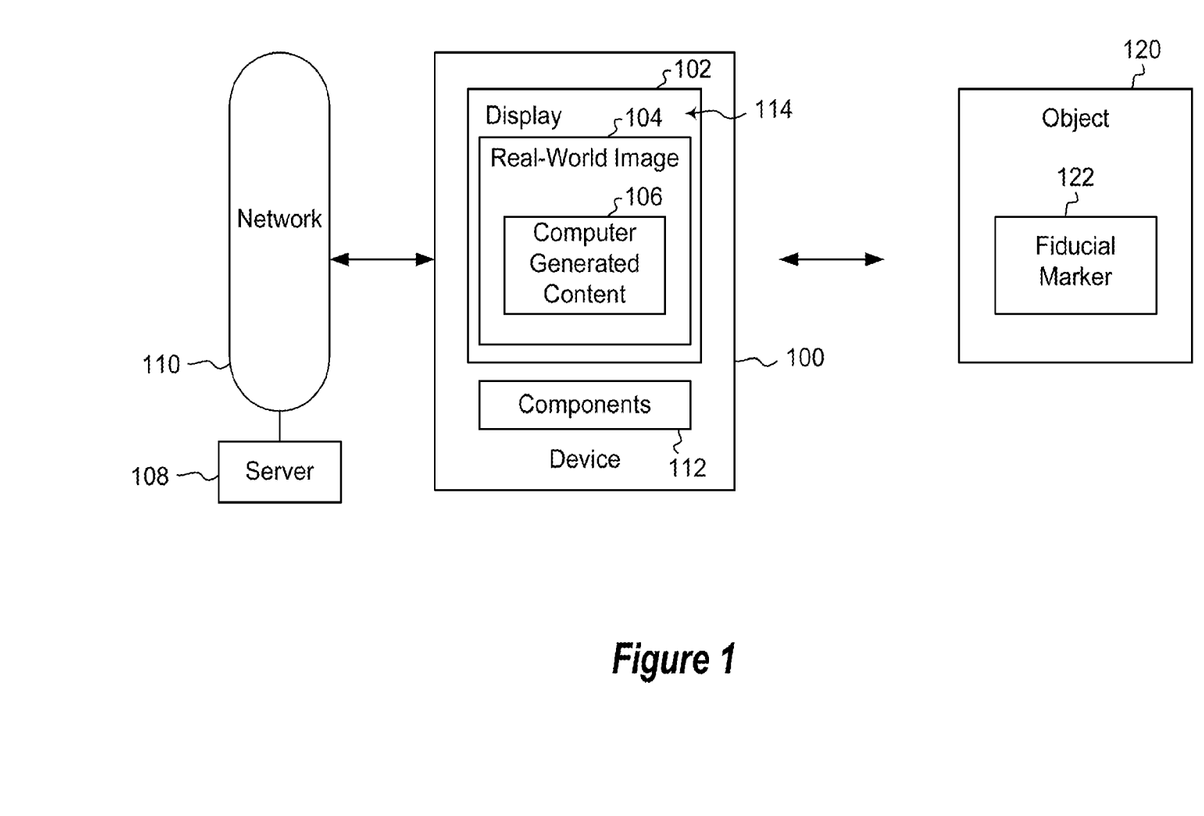
FIG. 1 illustrates an example of an environment that includes fiducial markers located in space.

FIG. 1 illustrates an example of an environment that includes fiducial markers located in space. In FIG. 1, a fiducial marker 122 has been placed on an object 120. The fiducial marker 122 can be placed unobtrusively and may be configured to be aesthetically compatible with the object 120. The size of the fiducial marker 122 may depend on the amount of data that is to be stored therein. This allows environmental concerns (e.g., impact of the fiducial marker on the environment) to be balanced with the size of the fiducial marker 122.

The fiducial marker 122 may have be on the scale of one inch square—however better printing processes can shrink them dramatically. Effective query distances can range, by way of example only and not limitation, from one inch to more than a mile depending on the sensitivity of the receiver—for example through a telescopic imager. One of skill in the art can appreciate that the fiducial marker 122 can be on the scale of one inch square, or larger, or smaller. The reading distance may depend on the sensitivity of the receiver.

FIG. 1 also illustrates a device 100 that includes a display 102. The device 100 may include an imaging system (e.g., a camera or a video-camera) that enables the device 100 to display or show a real-world image 104 of the object 120. The display 102 also presents computer-generated content 106 in the real-world image 104. Together, the real-world image 104 and the computer-generated content 106 is an example of an augmented image 114.

The computer-generated content 106 can be displayed in various ways and in various forms. The computer-generated content 106 (and thus the augmented image 114) may include text, images, video, color, highlights, or the like or any combination thereof. The real-world image 104 may be a real-time image of whatever is captured by the camera (or other input) of the device 100. As the device 100 moves and the view of the device 100 changes, the real-world image 100 displayed by the device 100 changes accordingly. Where applicable, the positioning of the computer-generated content 106 in the augmented image 114 may be updated in accordance with the movement of the device 100.

The computer-generated content 106 can be presented such that both the real-world image 104 and the computer-generated content 106 are simultaneously visible. Thus, at least one of the real-world image 104 and the computer-generated content 106 is partially transparent in one example. In another example, the computer-generated content 106 can be placed in specific portions of the display 102 such that portions of the real-world image 104 are completely obscured by the computer-generated content. Text, for example, can be placed directly on the image 104 of the object 120 in the display 102 or on the bottom of the display 102 so as to minimally interfere with the real-world image 104.

In FIG. 1, the device 100 includes components 112 that are used to generate and display the augmented image 114. The components 112 include, by way of example only, a camera, a compass, a global positioning sensor, or the like or any combination thereof. The components 112 can be used by the device 100 to generate the augmented image 114. For instance, the location of the device 100 and the orientation of the device 100 relative to the location of the object 120 can determined, respectively, by the GPS sensor and the compass and can be used in the generation of the computer-generated content 106. In some instances, the fiducial marker 122 may store location data. This location data, combined with data from the GPS sensor and/or compass can be used to locate the user relative to the object 120 and/or to generate the computer-generated content 106.

In some instances, the device 100 may communicate with a server 108 over a network 110, such as a telephone network, the Internet, a local-area network, or the like or any combination thereof. Information generated, detected, or otherwise determined by the components 112 can be transmitted to the server 108 and used in generating the augmented image 114. The information determined by the components 112 can also be used directly by the device 100 and may not be transmitted to the server 108.

For instance, information read from the fiducial marker 122 can be transmitted to the server 108. The server 108 can reply to the device 100 with at least some of the computer-generated content 106. In addition, the global positioning sensor may provide a location to the server 108. The location determined by the global positioning sensor and the data read from the fiducial marker 122 can be combined to generate the computer-generated content 106 and/or display the computer-generated content 106. Alternatively, at least some of the data used to generate the augmented image 114 may be stored locally on the device 100. Also, the data represented in the computer-generated content 106 may be wholly read from the fiducial marker 122.

The device 100 is configured to read the fiducial marker 122. Data stored by the fiducial marker 122 or data made accessible by the fiducial marker 122 can be rendered in the computer-generated content 106. For example, the fiducial marker 122 may store a description of the object 120. If the object 120 is a monument, for example, the fiducial marker 122 may store the date of creation, name of the artist, a reason for the monument, a description of the monument, or the like. If the object 120 is a business, the fiducial marker 122 may store contact information such as telephone numbers. One of skill in the art can appreciate that the data stored by or encoded in the fiducial marker 122 can vary widely. In addition, the format of the fiducial marker 122 can be standardized to enable any properly provisioned device to read and understand the data stored by the fiducial marker 122.

In one embodiment, the fiducial marker 122 may store a link (e.g., a Uniform Resource Locator (URL)) that can be used by the device 100 to access data from the server 108. This example effectively allows the fiducial marker 122 to be updated over time and also increases the effective amount of data that can be stored or made accessible by the fiducial marker 122. Once the device 100 has accessed the server 108, the corresponding data received from the server 108 includes the computer-generated content 106. This enables the augmented image 114 to include different types of data or to include different data at different times. The data that can be provided by the server 108 can be changed over time, or adapted to specific device configurations, or the like. For instance, the server 108 may also receive data describing the configuration (e.g., screen size, resolution, etc.) of the device. This allows the server 108 to deliver computer-generated content that is specifically prepared for the requesting device.

Figure 2:
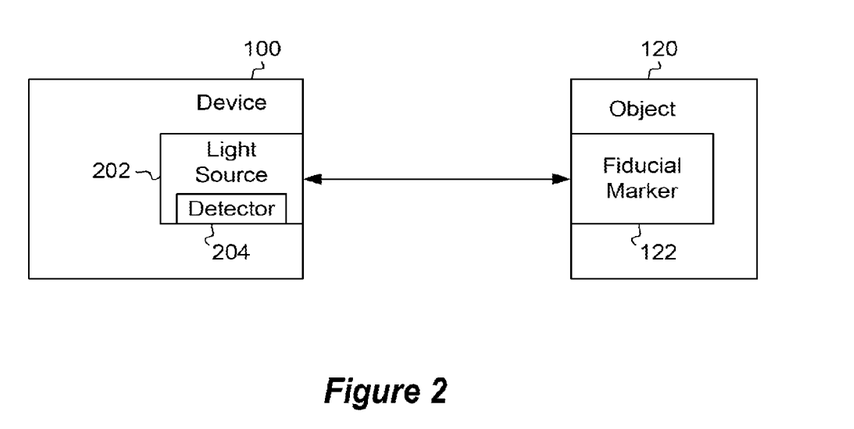
FIG. 2 illustrates an example of a device reading a fiducial marker that is attached to an object.

FIG. 2 illustrates an example of the device 100 reading the fiducial marker 122. The components 112 of the device 100 may also include a light source 202 and a light detector 204. The light source 202 is configured to emit a light beam. The light source 202 may include a laser, for example, that emits light at a predetermined frequency or within a predetermined frequency range. The detector 204 may be configured to detect the frequency of the light emitted by the light source 202. The detector 204 may be a photodetector such as a photodiode or the like.

In FIG. 2, the light emitted by light source 202 of the device 100 is directed towards the object 100 and more specifically towards the fiducial marker 122. The fiducial marker 122 reflects the light back toward the device 100. The device 100 detects the reflected light with the detector 204 to read the data stored in the fiducial marker 122.

In one example, the detector 204 can detect the intensity of the reflected light and generate a waveform that is shaped according to a mask pattern in the fiducial marker 122. The generated waveform can then be decoded and used to generate the computer-generated content 106 that is included in the augmented image 114.

The fiducial marker 122 may be or include a retroreflector that reflects light back towards its source. In this example, the fiducial marker 122 reflects light emitted by the light source 202 back towards the detector 204. More generally, the fiducial marker 122 reflects electromagnetic radiation back along a vector that is parallel or substantially parallel to the source of the electromagnetic radiation. As described in more detail herein, the fiducial marker 122 may include corner cubes, photonic crystals, a cat's eye retroreflector, or the like or any combination thereof.

Figure 3:
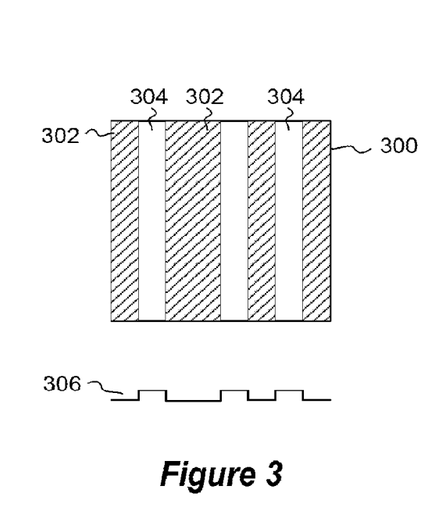
FIG. 3 shows an illustrative embodiment of a fiducial marker.

FIG. 3 shows an illustrative embodiment of a fiducial marker 300. The fiducial marker 300 is an example of the fiducial marker 122. In this example, the fiducial marker 300 is arranged in a single dimension. The fiducial marker 122 includes reflective areas 304 and less or non-reflective areas 302. When the light source 202 reads the fiducial marker 122, the detector 204 may generate a waveform 306 that corresponds to the pattern formed by the reflective areas 304 and the less or non-reflective areas 302. Simple passive reading of the fiducial marker 300 (or of other fiducial markers disclosed herein) can be accomplished by optically observing ambient reflected light. Alternatively a beam of light can be actively scanned over the fiducial marker 300 in a raster-scan like technique. Either approach can prove effective at both close range and distances of over a mile. However, greater distances may require both greater illumination energy and size of the fiducial marker 300.

The fiducial marker 300 can be fabricated in different ways. The fiducial marker 300 may include a sheet of corner cube reflectors. However, a mask may be applied to the surface of the sheet to form the less or non-reflective areas 302. Alternatively, the less or non-reflective areas 302 may not include corner cube reflectors.

The fiducial marker 300 can be read using raster-scanning techniques. For example, the light source may be a focused laser to read the data in the fiducial marker 300.

Figure 4:
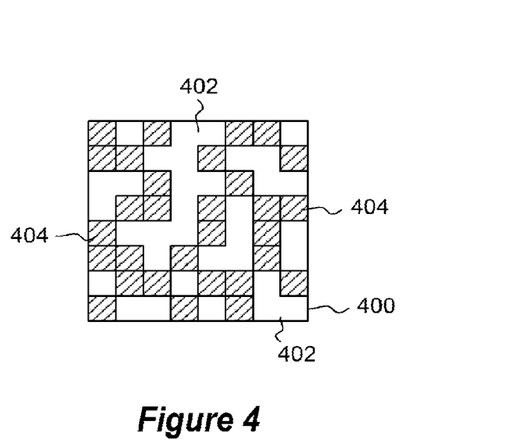
FIG. 4 shows another illustrative embodiment of a fiducial marker.

FIG. 4 shows another illustrative embodiment of a fiducial marker 400. The fiducial marker 400 is another example of the fiducial marker 122 and stores or codes data in multiple dimensions. The fiducial marker 400 includes reflective areas 402 and less or non-reflective areas 404. In this example, the data stored or represented by the fiducial marker 400 can be read with a dispersed laser that can illuminate the area of the fiducial marker or portions of the fiducial marker 400. The multi-dimensional area of the fiducial marker 400 can be read out in parallel in this example with a suitable light source. The multi-dimensional coding of the fiducial marker 400 can encode significantly more information for a given size of the fiducial marker 400. Multi-dimensional coding allows a fixed size marker 400 to encode more information and/or the use of a smaller fiducial marker. Even a smaller multi-dimensional marker may store more data than a larger single dimensional fiducial marker. This mulit-dimensional approach further enables parallel readout. For example, two illumination sources can be used to read out the data from the first two rows at the same time.

In comparison, the fiducial marker 400 can store more data than the fiducial marker 300 and thus occupy less area. This may be useful, for instance, when placing fiducial markers on objects in the environment.

Figure 5:
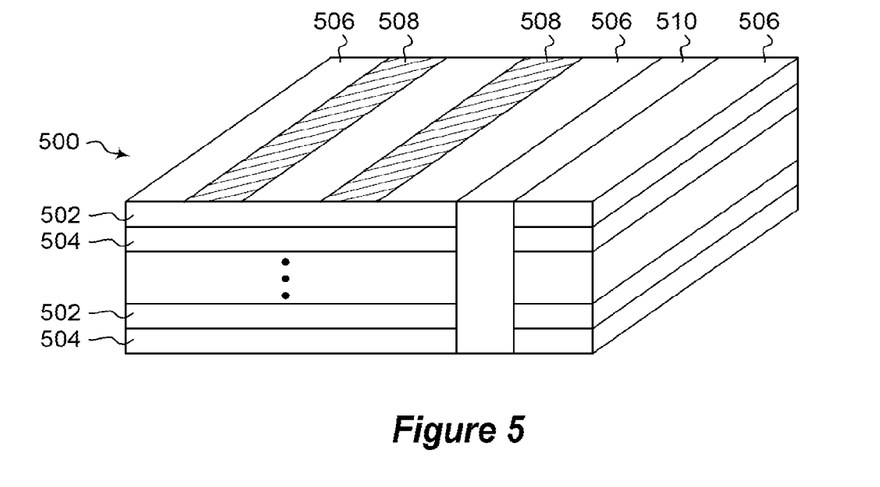
FIG. 5 shows an illustrative embodiment of a fiducial marker that is manufactured using photonic crystals.

FIG. 5 shows an illustrative embodiment of a fiducial marker 500 that is manufactured from photonic crystals. The fiducial marker 500 is another example of the fiducial marker 122. In this example, the fiducial marker 500 is formed from multiple layers 502 and 504. The layer 502 has an index of refraction that is different from an index of refraction of the layer 504. The layers 502 and 504 depict alternating layers of materials having high and low indices of refraction or high and low dielectric constants. The layers 504 and 504 may be formed or grown on a substrate. Examples of suitable materials include silicon, plastic, and some semi-rigid gels. The thickness of each of the layers 502 and 504, for example, may be configured for specific frequencies of light. In some examples, the thickness of each of the layers 502 an 504 is one-fourth of the desired wavelength.

The proper selection of materials for the layers 502 and 504 result in a structure that reflects certain frequencies of light. As a result, the fiducial marker 500 can reflect light from a source back to the source. The fiducial marker 500 can be constructed to provide unidirectional readout without the need to align the illumination source with the fiducial marker 500 in any way.

Encoding data in the fiducial marker 500 can be achieved by providing a mask 508. By masking a part of the surface of the fiducial marker 500 according to a pattern, data can be encoded and read by a device. In this example, the mask 508 may include an additional layer of material that is selectively formed on the surface of the fiducial marker 500. For example, the mask 508 may be a metallic layer. The area 506 is reflective and may not have the mask 508. In some examples, the fiducial marker 500 may have a protective layer formed on top of the fiducial marker 500 that does not interfere with the operation or function of the fiducial marker 500.

FIG. 5 also illustrates that the mask can be formed by etching the fiducial marker 500. For example, the fiducial marker 500 can be etched and another material 510 can be deposited in the etched area of the fiducial marker 500 to form the mask and create a pattern in the fiducial marker 500. The material 510 may not include alternating layers or may be of a material that is non-reflective for certain wavelengths of light such that the relevant frequency or wavelength of light is not reflected for the portion of the fiducial marker 500 occupied by the material 510.

Figure 6:
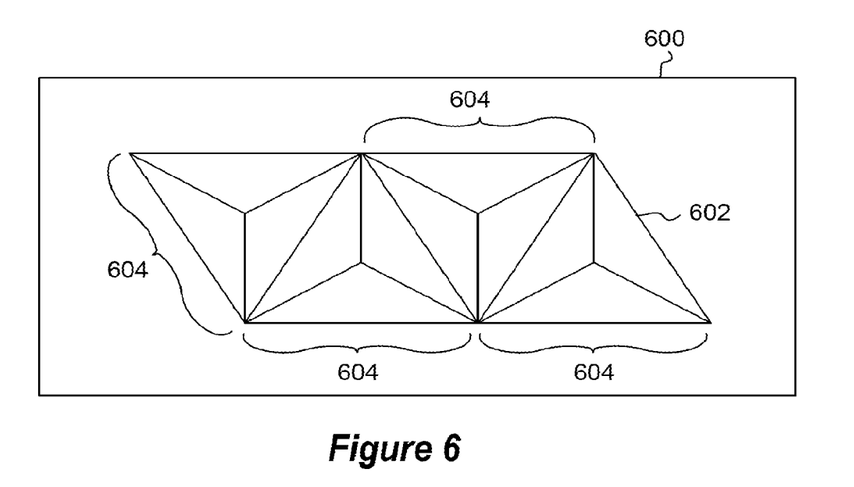
FIG. 6 shows an illustrative embodiment of a fiducial marker that includes an array of retroreflectors.

FIG. 6 shows an illustrative embodiment of a fiducial marker 600 that includes an array 602 of retroreflectors. The fiducial marker 600 is an example of the fiducial marker 122. In this example, the array 602 of retroreflectors includes corner cubes 604. The array 602 can include multiple rows and/or columns of corner cubes 604. The array 602 of corner cubes 604 may be formed using molded plastic. Each of the corner cubes 604 typically includes three mutually perpendicular, intersecting flat surfaces, which reflect electromagnetic radiation, including light, back towards the source.

The fiducial marker 600, once placed in an environment, can be read from different positions or locations. In other words, light that approaches the fiducial marker 600 from the front or at an angle is reflected back to the location of the source of the light. As a result, the orientation of the fiducial marker 600 may not impact the ability of the fiducial marker 600 to be read by a device. The fiducial marker 600 may also include a mask to form a pattern that stores data. The mask can be formed by obscuring some of the corner cubes 604 or by manufacturing the array 602 such that certain areas are devoid of corner cubes.

Figure 7:
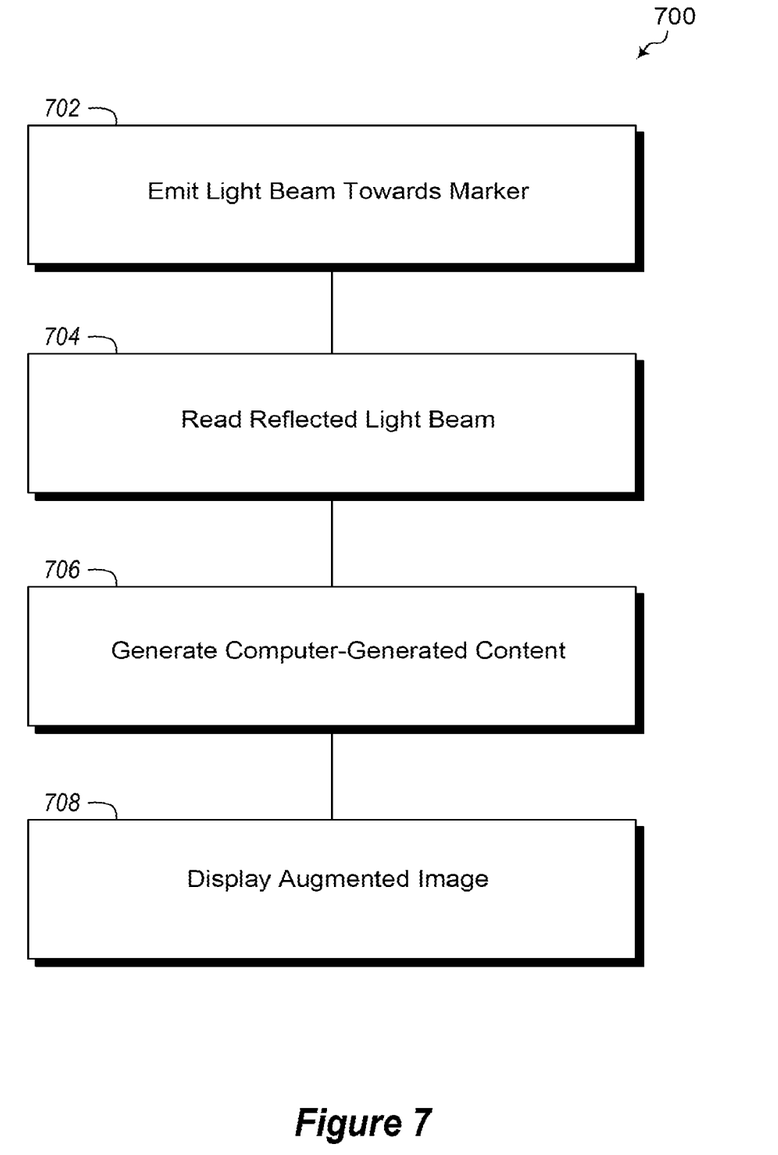
FIG. 7 shows an illustrative embodiment of a method for generating an augmented image using a fiducial marker.

FIG. 7 shows an illustrative embodiment of a method 700 for generating an augmented image. In block 702 of the method 700, a light beam is emitted by a device towards a fiducial marker. The light source may be configured to scan the fiducial marker or the device can be moved such that the emitted light can interrogate the fiducial marker.

In block 704, the device detects and reads the reflected light beam. The reflected light beam is typically modulated according to the mask or pattern of the fiducial marker. The reflected light beam thus contains the data stored by the fiducial marker.

In block 706, the data in the reflected light beam is used to generate computer-generated content to include in the augmented image. In one example, the computer-generated content corresponds to the data stored in the fiducial marker. In another example, the data stored in the fiducial marker may enable the device to access (e.g., over the Internet) the computer-generated content that is associated with the fiducial marker. In block 708, the augmented image, which includes the computer-generated content and/or an image of a real world object, is displayed on the device.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 8:
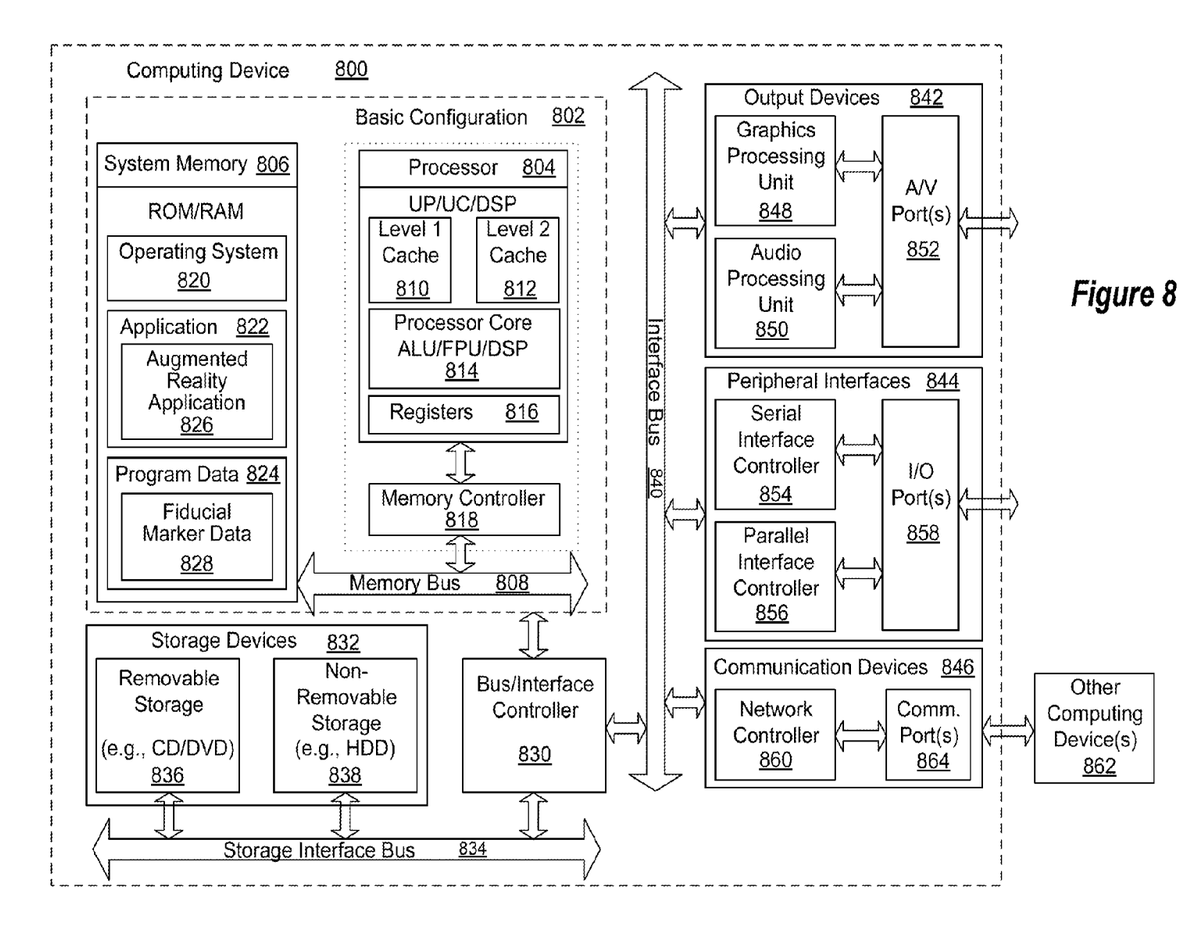
FIG. 8 is a block diagram illustrating an example computing device that is arranged for reading a fiducial marker and generating augmented images using the data read from the fiducial marker.

FIG. 8 is a block diagram illustrating an example computing device 800 that is arranged for reading a fiducial marker and generating augmented images using the data read from the fiducial marker in accordance with the present disclosure. In a very basic configuration 802, computing device 800 typically includes one or more processors 804 and a system memory 806. A memory bus 808 may be used for communicating between processor 804 and system memory 806.

Depending on the desired configuration, processor 804 may be of any type including but not limited to a microprocessor (μP), a microcontroller (μC), a digital signal processor (DSP), or any combination thereof. Processor 804 may include one more levels of caching, such as a level one cache 810 and a level two cache 812, a processor core 814, and registers 816. An example processor core 814 may include an arithmetic logic unit (ALU), a floating point unit (FPU), a digital signal processing core (DSP Core), or any combination thereof. An example memory controller 818 may also be used with processor 804, or in some implementations memory controller 818 may be an internal part of processor 804.

Depending on the desired configuration, system memory 806 may be of any type including but not limited to volatile memory (such as RAM), non-volatile memory (such as ROM, flash memory, etc.) or any combination thereof. System memory 806 may include an operating system 820, one or more applications 822, and program data 824. Application 822 may include an augmented reality application 826 that is arranged to produce and display content that is read from or made accessible by reading a fiducial marker. Program data 824 may include fiducial marker data 828 read from the fiducial marker that may be useful for generating augmented images as is described herein. The fiducial marker data 828 may also include other data that may be used in generating augmented images. In some embodiments, application 822 may be arranged to operate with program data 824 on operating system 820 such that an augmented image is generated and displayed. This described basic configuration 802 is illustrated in FIG. 8 by those components within the inner dashed line.

Computing device 800 may have additional features or functionality, and additional interfaces to facilitate communications between basic configuration 802 and any required devices and interfaces. For example, a bus/interface controller 830 may be used to facilitate communications between basic configuration 802 and one or more data storage devices 832 via a storage interface bus 834. Data storage devices 832 may be removable storage devices 836, non-removable storage devices 838, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 806, removable storage devices 836 and non-removable storage devices 838 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 800. Any such computer storage media may be part of computing device 800.

Computing device 800 may also include an interface bus 840 for facilitating communication from various interface devices (e.g., output devices 842, peripheral interfaces 844, and communication devices 846) to basic configuration 802 via bus/interface controller 830. Example output devices 842 include a graphics processing unit 848 and an audio processing unit 850, which may be configured to communicate to various external devices such as a display or speakers via one or more A/V ports 852. Example peripheral interfaces 844 include a serial interface controller 854 or a parallel interface controller 856, which may be configured to communicate with external devices such as input devices (e.g., keyboard, mouse, pen, voice input device, touch input device, etc.) or other peripheral devices (e.g., printer, scanner, etc.) via one or more I/O ports 858. An example communication device 846 includes a network controller 860, which may be arranged to facilitate communications with one or more other computing devices 862 over a network communication link via one or more communication ports 864.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 800 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 800 may also be implemented as a personal computer including both laptop computer and non-laptop computer configurations.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A fiducial marker comprising:
a sheet of a material attached to an object, the material having a first portion and a second portion, the material configured to reflect electromagnetic radiation; and
a mask applied to the material, wherein the mask obscures the first portion of the material and not the second portion of the material;
wherein the first portion and the second portion store data to be read by a device and displayed by the device with a real-time image of the object.

2. The fiducial marker of claim 1, wherein the material includes a plurality of corner cubes.

3. The fiducial marker of claim 1, wherein the material includes at least one photonic crystal.

4. The fiducial marker of claim 3, wherein the photonic crystal comprises a multi-dimensional photonic crystal.

5. The fiducial marker of claim 1, wherein the first portion of the material and the second portion of the material are arranged to convey data to a device when read by the device, wherein light emitted by the device is reflected back to the device in accordance with the mask such that data stored in the material can be read by the device.

6. The fiducial marker of claim 1, wherein the first portion and the second portion of material store data that is at least one of: descriptive of the object; a reference for scaling of the object; correlates the object with a second object; provides a relative scale when comparing a location of the fiducial marker with a second fiducial marker; or a uniform resource locator that enables the device to access computer-generated content over a network.

7. The fiducial marker of claim 1, wherein the electromagnetic radiation includes light and wherein the second portion of the material comprises a retroreflector that reflects the light back to a source of the light.

8. The fiducial marker of claim 1, wherein the fiducial marker is readable by the device from more than a mile away from the fiducial marker.

9. The fiducial marker of claim 1, wherein the first portions and the second portions collectively form a one-dimensional barcode.

10. The fiducial marker of claim 1, wherein the first portions and the second portions collectively form a two-dimensional barcode.

11. A method for augmenting a real-world image with a computer-generated image, the method comprising:
emitting a light beam towards a tangible fiducial marker located on a real-world object;
reading a reflected light beam from the tangible fiducial marker, wherein the reflected light beam includes data stored by the tangible fiducial marker;
generating computer-generated content using the data, the computer-generated content related to the real-world object; and
displaying an augmented image on a display of a device, wherein the augmented image includes the computer-generated content and a view of the real-world object.

12. The method of claim 11, wherein the light beam comprises a laser beam, further comprising scanning the tangible fiducial marker with the laser beam.

13. The method of claim 11, wherein the tangible fiducial marker comprises a plurality of retroreflectors arranged to store the data and arranged to generate the reflected light beam.

14. The method of claim 11, wherein the data includes a uniform resource locator, further comprising accessing a server using the uniform resource locator for the computer-generated content.

15. The method of claim 11, wherein reading a reflected light beam from the tangible fiducial marker further comprises demodulating a signal generated from the reflected light beam to extract the stored data.

16. The method of claim 11, further comprising using additional components of the device to generate the computer-generated content, the additional components including a global positioning sensor and a compass.

17. The method of claim 11, wherein the tangible fiducial marker comprises a plurality of corner cubes arranged in an array, wherein at least one of:
a portion of the plurality of corner cubes are obscured such that the array of the plurality of corner cubes stores the data that can be read by the light beam; or
a portion of the array is devoid of corner cubes such that the plurality of corner cubes and the portion of the array devoid of corner cubes are arranged to be read by the light beam.

18. The method of claim 11, wherein the tangible fiducial marker comprises a photonic crystal having a mask formed thereon to form a reflective portion and a less or non-reflective portion, wherein the reflective portion and the less or non-reflective portion are arranged to store the data.

19. The method of claim 11, wherein the real-world object comprises a monument and the computer-generated content comprises at least one of a date of creation of the monument, a name of an artist of the monument, a reason for the monument, or a description of the monument.

20. The method of claim 11, wherein the real-world object comprises a business and the computer-generated content comprises contact information of the business.

21. The method of claim 11, wherein the tangible fiducial marker comprises retro reflective paint painted on the real-world object according to a pattern.

22. A fiducial marker comprising:
a material attached to an object in an environment, the material including:
   a first portion having a retroreflector configured to reflect electromagnetic radiation received from a device back towards the device; and
   a second portion that is less or non-reflective, wherein the first portion and the second portion are arranged to form a pattern to store data;
wherein electromagnetic radiation reflected by the material is modulated according to the pattern and wherein the reflected electromagnetic radiation is configured to be detected and read by a device that emitted the electromagnetic radiation towards the first and second portions and displayed by the device with a real-time view of the environment.

23. The fiducial marker of claim 22, wherein the retroreflector comprises at least one of: a plurality of corner cubes arranged in an array or a photonic crystal.

24. The fiducial marker of claim 23, wherein the second portion comprises a mask that is applied to the material to a portion of the plurality of corner cubes or the photonic crystal.

25. The fiducial marker of claim 23, wherein the second portion is devoid of retroreflectors.

26. The fiducial marker of claim 22, wherein the data is at least one of:
descriptive of the object;
a uniform resource locator that enables the device to access computer-generated content to include in an augmented image displayed on the device over a network; or
used to generate the computer-generated content.

* * * * *

UNITED STATES PATENT AND TRADEMARK OFFICE
CERTIFICATE OF CORRECTION

| | |
|---|---|
| PATENT NO. | : 8,434,674 B2 |
| APPLICATION NO. | : 13/058831 |
| DATED | : May 7, 2013 |
| INVENTOR(S) | : Mangione-Smith |

It is certified that error appears in the above-identified patent and that said Letters Patent is hereby corrected as shown below:

On the title page, item (56), "OTHER PUBLICATIONS", in Column 2, Line 8, delete "Astonomical" and insert -- Astronomical --, therefor.

On title page 2, item (56), "OTHER PUBLICATIONS", in Column 2, Line 11, delete "15 663-672," and insert -- 15, pp 663-672, --, therefor.

On title page 2, item (56), "OTHER PUBLICATIONS", in Column 2, Line 15, delete "3 713-720," and insert -- 3, pp 713-720, --, therefor.

In the Drawings

In Fig. 8, Sheet 5 of 5, delete "UP/UC/DSP" and insert -- μP/μC/DSP --, therefor.

In the Specifications

In Column 2, Line 18, delete "can is read. from" and insert -- can be read. From --, therefor.

In Column 3, Line 58, delete "material" and insert -- material. --, therefor.

In the Claims

In Column 14, Lines 9-10, in Claim 9, delete "first portions and the second portions" and insert -- first portion and the second portion --, therefor.

In Column 14, Lines 12-13, in Claim 10, delete "first portions and the second portions" and insert -- first portion and the second portion --, therefor.

Signed and Sealed this
Twenty-second Day of October, 2013

Teresa Stanek Rea
*Deputy Director of the United States Patent and Trademark Office*

Figure 8

UNITED STATES PATENT AND TRADEMARK OFFICE
CERTIFICATE OF CORRECTION

PATENT NO. : 8,434,674 B2  Page 1 of 1
APPLICATION NO. : 13/058831
DATED : May 7, 2013
INVENTOR(S) : William H. Mangione-Smith It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 63 days.

Signed and Sealed this
Eighth Day of September, 2015

Michelle K. Lee
*Director of the United States Patent and Trademark Office*